(12) United States Patent
Zhao et al.

(10) Patent No.: US 9,746,403 B2
(45) Date of Patent: Aug. 29, 2017

(54) METHOD OF TESTING A POLYCRYSTALLINE DIAMOND COMPACT CUTTER

(71) Applicant: CNPC USA CORPORATION, Houston, TX (US)

(72) Inventors: Liang Zhao, Spring, TX (US); Xiaomin Cheng, Houston, TX (US); Xueqing Teng, Korla (CN)

(73) Assignee: CNPC USA CORP., Houston, TX (US)

( * ) Notice: Subject to any disclaimer, the term of this patent is extended or adjusted under 35 U.S.C. 154(b) by 56 days.

(21) Appl. No.: 14/873,564

(22) Filed: Oct. 2, 2015

(65) Prior Publication Data

US 2016/0097702 A1 Apr. 7, 2016

Related U.S. Application Data

(60) Provisional application No. 62/060,271, filed on Oct. 6, 2014.

(51) Int. Cl.
| | |
|---|---|
| *G01N 3/08* | (2006.01) |
| *E21B 10/56* | (2006.01) |
| *G01N 3/04* | (2006.01) |
| *G01N 3/58* | (2006.01) |

(52) U.S. Cl.
CPC ............ *G01N 3/08* (2013.01); *E21B 10/56* (2013.01); *G01N 3/04* (2013.01); *G01N 3/58* (2013.01)

(58) Field of Classification Search
CPC .. G01N 3/04; G01N 3/08; E21B 10/43; E21B 10/55; E21B 10/46; E21B 10/56
USPC .......................................................... 73/799
See application file for complete search history.

(56) References Cited

U.S. PATENT DOCUMENTS

| | | | | |
|---|---|---|---|---|
| 5,265,685 | A | * | 11/1993 | Keith ................... E21B 10/04 175/431 |
| 6,651,757 | B2 | | 11/2003 | Belnap et al. |
| 6,659,199 | B2 | * | 12/2003 | Swadi .................. E21B 10/46 175/431 |
| 7,866,413 | B2 | | 1/2011 | Stauffer et al. |
| 8,130,903 | B2 | | 3/2012 | Corbett et al. |
| 8,322,217 | B2 | | 12/2012 | Bellin |
| 8,404,019 | B2 | | 3/2013 | Ladi et al. |
| 8,875,812 | B2 | * | 11/2014 | Setlur .................. B22F 7/08 175/379 |

(Continued)

*Primary Examiner* — Lisa Caputo
*Assistant Examiner* — Octavia Hollington
(74) *Attorney, Agent, or Firm* — Ramey & Schwaller, LLP (57) ABSTRACT

The method for determining fracture toughness includes clamping a cutting element in a first orientation, exerting a confining pressure on the cutting element, applying a first load at a first distance from a perimeter of the diamond table of the cutting element, increasing the first load to a first level sufficient to fracture, and recording the first level sufficient to fracture. Then, another load is applied at another distance from a perimeter of the diamond table with another cutting element or the same cutting element in another orientation. The load is increased until fracture again. The steps are repeated at different distances and different orientations to create a profile of the fracture toughness of the cutting element. The method also includes wearing the cutting element and measuring fracture toughness at a worn distance. The profile is a more complete rating of the cutting element under drilling conditions.

20 Claims, 4 Drawing Sheets

(56) References Cited

U.S. PATENT DOCUMENTS

| | | | |
|---|---|---|---|
| 9,284,790 B2* | 3/2016 | Zhang | E21B 10/56 |
| 2004/0143427 A1 | 7/2004 | Huang et al. | |
| 2006/0042171 A1 | 3/2006 | Radtke et al. | |
| 2013/0239652 A1 | 9/2013 | Pelfrene et al. | |
| 2015/0275584 A1* | 10/2015 | Mensa-Wilmot | E21B 10/43 |
| | | | 175/431 |
| 2016/0097242 A1* | 4/2016 | Zhao | E21B 10/573 |
| | | | 175/432 |

* cited by examiner

METHOD OF TESTING A POLYCRYSTALLINE DIAMOND COMPACT CUTTER

CROSS-REFERENCE TO RELATED APPLICATIONS

The present application claims priority under 35 U.S.C. Section 119(e) from U.S. Provisional Patent Application Ser. No. 62/060,271, filed on 6 Oct. 2014, entitled "METHOD FOR TESTING A POLYCRYSTALLINE DIAMOND COMPACT CUTTER".

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OM MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

The present invention relates to polycrystalline diamond compact cutters on a drill bit. More particularly, the present invention relates to measuring fracture toughness of a polycrystalline diamond compact cutter. The present invention also relates to rating polycrystalline diamond compact cutters for fracture toughness.

2. Description of Related Art Including Information Disclosed Under 37 CFR 1.97 and 37 CFR 1.98

Diamond is the hardest material known, so cutters of diamond composition have been pursued. Drill bits were tipped with diamond for improved cutting efficiency through rock formations. Bonding diamond to metal is a challenge, so the drill bits evolved from steel to composite materials, in particular, tungsten carbide. Tungsten carbide composite readily bonds to diamond. Polycrystalline diamond compact (PDC) cutters are diamond tipped protrusions on the drill bit. The PDC cutters form the cutting surface of the drill bit with diamond, while the drill bit can be comprised of other materials. PDC cutters are commonly used in drilling operations for oil and gas.

A basic PDC cutter is comprised of a diamond table made from diamond grit with binder and a substrate of tungsten carbide and metallic binder, usually cobalt. The diamond grit is sintered under high temperature and high pressure conditions, forming a layer bonded to the tungsten carbide or other substrate. The High Temperature-High Pressure (HT-HP) press can form the layer with a Cobalt or other Group VIII element as the catalyst binder, and the properties of the layer have been modified for various thicknesses, profiles, and patterns to affect the working life of the cutters.

The PDC cutter is further processed to withstand the downhole conditions of extreme pressures and high temperatures. Excessive heat, over 750 degrees Celsius, causes thermal expansion of the diamond-binder bond in the diamond table, causing changes to the integrity of the cutter. To reduce the susceptibility to high temperatures, the cutter is subjected to a leaching process, which removes metallic binder from the diamond table using acid. Selective leaching removes the binder, usually cobalt, in different percentages through the volume of the diamond table so that the cutter is resistant to thermal expansion. However, the selective leaching affects other properties of the cutter, such as fracture toughness. Even though the cutter is more resistant to thermal expansion, the cutter may be less tough.

Once sintered and leached, it is important to verify the actual physical tolerances of the cutter. It is necessary to measure the fracture toughness of a cutter after manufacture, so that the appropriate cutter can be selected for a particular drill bit or for a particular position on the drill bit. A batch of cutters formed through the same sintering process and leaching process can be rated for particular fracture toughness by testing one representative cutter from the batch.

Figure 1:
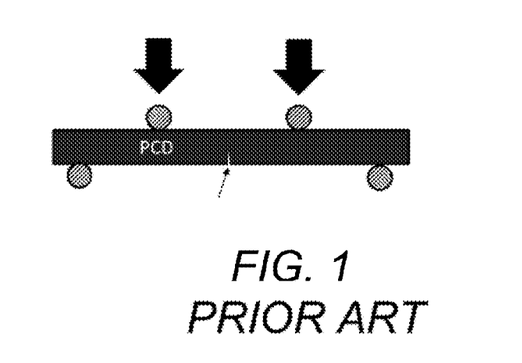
FIG. 1 is a schematic view of a prior art method of determining fracture toughness.

In the prior art, the method of testing fracture toughness is 3-point bending and/or 4-point bending, wherein a notch is formed on the diamond table and the amount of force to crack the cutter is found. FIG. 1 shows the method of 4-point bending with four transverse forces exerted against the diamond table surface with an induced crack. The amount of transverse force, such as the amount of weight, needed to fracture the diamond table, sets a fracture toughness measurement or K1C measurement. There are already industrial standards and tables for fracture toughness, such as ASTM (American Society for Testing and Materials International) standards, which have been developed based on this prior art method.

Various patents have issued and various applications have been published in the field of measuring PDC compact cutters.

U.S. Pat. No. 6,651,757, issued to Belnap, et al. on Nov. 25, 2003, discloses the known "drop hammer" and "3 point bending" method. Hardness is tested using a Vicker's indenter with a 500 gram load on a conventional micro-hardness testing apparatus. Measurements are taken of the impressions made on the PDC surface made by the indenter and the load. Another testing embodiment is an impact test. An insert is placed in a rigid fixture and a specific weight is dropped on it from predetermined heights. The "impact resistance" is determined as the maximum "drop height" that the insert can withstand prior to chipping or impact damage.

U.S. Pat. No. 8,322,217, issued to Bellin on Dec. 4, 2012, discloses an acoustic emissions testing device designed to determine the toughness of super hard materials. The device tests toughness by incorporating an acoustic sensor, in indenter coupled to a testing sample with a hard surface, and a load. When the load is exerted on the indenter, the force is transferred to the hard surface and the acoustic sensor detects acoustic events occurring within the testing sample. The acoustic emissions generated by the load upon the hard surface are recorded and stored for comparison to other testing samples to determine the relative toughness of those samples. The profile of acoustic emissions for a set of samples allows selection of a cutter with particular hardness.

U.S. Pat. No. 8,130,903, issued to Corbett, et al. on Mar. 6, 2012, discloses a non-destructive device and method for evaluating toughness. X-rays penetrate the sample and cause a target element, preferably a non-diamond material acting as a substrate, within the desired section of the sample to emit x-ray fluorescence. The profile of emitted fluorescence correlates to diamond content and toughness.

U.S. Pat. No. 8,404,019, issued to Ladi, et al. on Mar. 26, 2013, discloses another micro-hardness test for PDC surfaces within the context of determining the location and amount of leaching that has occurred in a PDC sample. A Lewis acid removes the metallic binder, and the solid metal in the solution is precipitated from the drained solution. The collected amount of metal indicates hardness and toughness of the cutter. United States Publication No. 20060042171, published for Radtke, et al. on Mar. 2, 2006, discloses a number of hardness tests to determine the impact resistance of ceramic impregnated superabrasives. These tests include the Knoop hardness test, a drop weight impact test, and the use of an Instron Instrumented Impact Test machine.

The prior art testing methods lack applicability in downhole conditions. The cutter does not experience such clean testing conditions downhole. For example, the cutter is not impacted straight on, but rather at an angle; and there are no induced cracks or notches on the cutter with the substrate.

Additionally, the cutter is known to have non-uniform residual stress from the formation process. After the high temperature-high pressure sintering process, there is a very high residual stress within the diamond table. The coefficient of thermal expansion of the tungsten carbide substrate is much higher than the coefficient of thermal expansion of the diamond. Given a non-planar interface on the substrate, the residual stress on the diamond table for bonding to an uneven amount of substrate would be non-uniform, after the sintering process. For diamond hard substances, the bond to the substrate is important in drilling operations, and it is known that the sintering process to bond is not uniform across the interface between the diamond table and the substrate. The prior art testing methods still only test at a center point and assume uniformity, when the formation of the PDC cutter for drilling operations conflicts with the assumption of uniformity.

It is an object of the present invention to provide a method for determining fracture toughness of a cutting element.

It is an object of the present invention to provide a method for determining fracture toughness of a cutting element at different positions on the surfaces of the cutting element.

It is an object of the present invention to provide a method for determining fracture toughness of a cutting element, when the cutting element is worn.

It is another object of the present invention to provide a method for rating fracture toughness of cutting elements for assembling a drill bit.

It is another object of the present invention to provide a method for compiling a profile of fracture toughness based on different positions on the cutting element. The profile provides information for the batch of cutters manufactured under the same conditions.

It is still another objection of the present invention to provide a method of selecting a cutting element according to the profile of fracture toughness.

These and other objectives and advantages of the present invention will become apparent from a reading of the attached specification.

BRIEF SUMMARY OF THE INVENTION

Embodiments of the method and device for determining fracture toughness according to the present invention can form a profile of fracture toughness of a cutting element. The profile will be associated with cutting elements manufactured under the same conditions, including the same batch of cutting elements. A more consistent and accurate rating of a cutting element can be available for assembling a drill bit. A cutting element is comprised of a diamond table and a substrate. The sintering and leaching processes do not create a uniform composition throughout the diamond table. The present invention discloses a method and device for testing more than a single middle point for fracture toughness of the prior art.

A method according to one embodiment includes clamping the cutting element into a fixture in a first orientation, exerting a confining pressure on the diamond table; applying a first load at a first distance from a perimeter of the first diamond table; increasing the first load to a first level sufficient to fracture the first diamond table; and recording the first level sufficient to fracture the first diamond table. A second load is applied at a second distance from a perimeter of a second diamond table with the cutting element in a second orientation. The first diamond table and the second diamond table are manufactured under the same conditions, including the same batch of cutters. The second load is increased to a second level sufficient to fracture the second diamond table, and the second level is recorded. Another load is applied at another distance from a perimeter of the diamond table with another cutting element in another orientation. Again, the other load is increased to another level sufficient to fracture the diamond table, and this other level is record. A fracture can be observed visually or non-visually. The steps of applying load, increasing load until fracture, and recording the load to fracture can be repeated at different distances from the perimeter of the diamond tables. A profile of the cutting element and all cutting elements manufactured under the same conditions can be compiled from data comprised of distance, load, and level sufficient to fracture the diamond table. The class of cutting elements, including the same batch can be rated for more informed selection and assembly of a drill bit.

In some embodiments, the same cutting element can be used for different distances from the perimeter. The orientation of the cutting element changes as the distance from the perimeter changes. The cutting element is released from the fixture and clamped in the second orientation for the second distance. The second orientation is spaced from the first orientation, such as rotating the cutting element at least 90 degrees. The fracture from the first orientation is isolated and the integrity of the cutting element is the same for the new second orientation as the first orientation before the fracture in the first orientation. The orientation can continue to change and the cutting element can continue to rotate for more than one fracture on a cutting element. The profile can now include data comprised of orientation, distance, load, and level sufficient to fracture the diamond table. The profile can still be used to rate cutting elements manufactured under the same conditions.

The present invention also includes an embodiment of the method, which accounts for wear on the cutting element. The cutting element can be worn between fractures, so that the fracture toughness more closely simulates drilling conditions. In the method before the step of applying the second load at the second distance, the cutting element is released from the fixture, and an edge of the cutting element is worn to a first worn distance. The worn cutting element is placed back into the fixture, and the second load is applied and increased to fracture the worn cutter. The worn edge is aligned at the second orientation, so that the fracture after the first load does not affect the fracture for the second load.

The orientation and the distance can be varied or kept the same for the cutting element with or without the worn edge. Additionally, the amount of worn distance can be varied for other loads and distances. The profile of the fracture toughness can now include data comprised of distance, orientation, worn distance, load, and level sufficient to fracture the diamond table.

Embodiments of the device for determining fracture toughness of the present invention includes a fixture holding a cutting element, a clamp mounted on the fixture with the cutting element set in the clamp, a means for exerting a confining pressure on the diamond table in the clamp, and a loading means at a first distance from a perimeter of the diamond table. The loading means applies and increases load at the different distances and different orientations of the cutting element. There can also be a means for wearing the edge of the cutting element, and a means for recording data comprised of distance, orientation, worn distance, load, and level sufficient to fracture the diamond table. The data is compiled to form a more complete profile of fracture toughness of a cutting element, having been formed by a particular sintering and leaching processes under particular conditions. Other cutting elements under the same sintering and leaching.

DETAILED DESCRIPTION OF THE INVENTION

Figure 2:
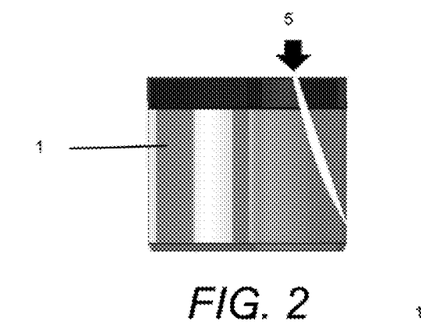
FIG. 2 is an elevation view of a cutting element fractured by impact force.
Figure 3:
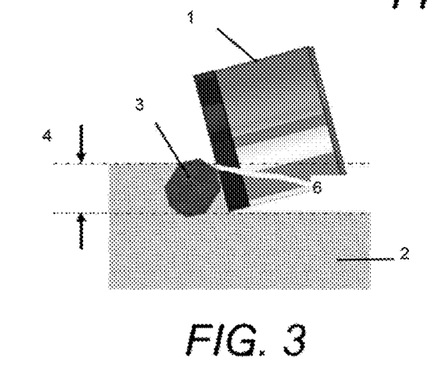
FIGS. 3 and 4 are schematic views of a cutting element interacting with nodules in a formation during a drilling operation.
Figure 4:
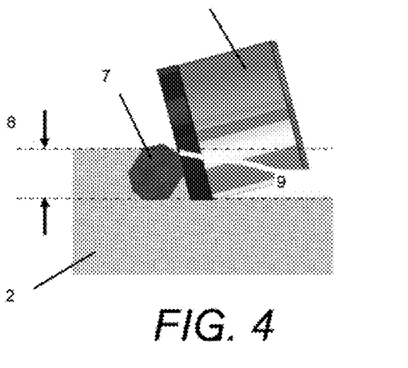
Figure 5:
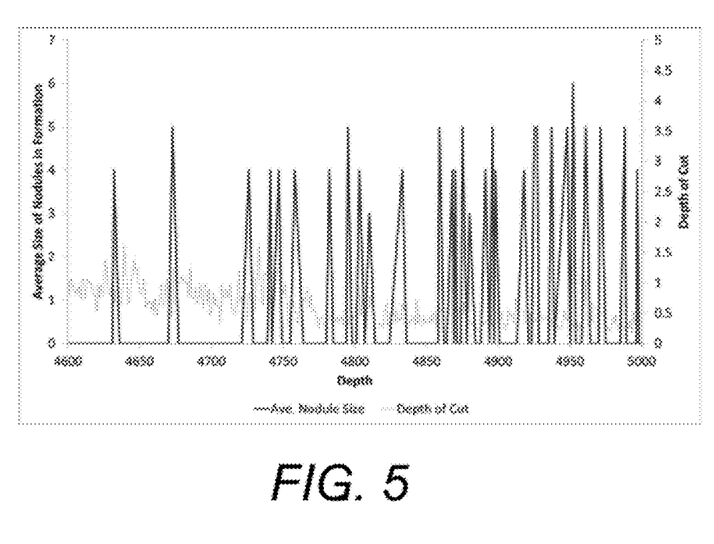
FIG. 5 is a graph illustration of the size of nodules and depth of the cutting element in relation to depth of the formation.

FIGS. 2-4 show a cutting element 1 being fractured in a drilling operation. FIG. 2 shows an impact force 5 exerted on the cutting element 1 at a top surface. The impact force 5 is not centered on the cutting element 1. FIG. 3 shows the cutting element 1 in the formation 2 and interacting with a nodule 3, such as a mineral or other deposit in the formation. The cutting element 1 is cutting to a depth 4, and the nodule 3 causes a fracture 6 through the cutting element 1. FIG. 4 shows an alternative cutting element 1 in the formation 2 and interacting with a different nodule 7 and cutting to a different depth 8. The cutting element 1 has a different fracture 9 under the different conditions. In the drilling operation, the top surface of the cutting element 1 interacts with impact forces at different distances from the perimeter toward the center. FIG. 5 is the graph illustration, showing the different interactions of depth of cutting and size of nodules, according to the depth of the formation. As the drill bit moves deeper into the formation, the depth of cutting changes and the impact forces of nodules changes.

FIG. 1 shows the prior art test for toughness being measured for fracture on a bottom side of only the diamond table of the cutting element. The measurement in FIG. 1 is also centered. The relevance of the toughness rating based on a prior art method, as in FIG. 1, relies on a positive correlation between fracturing at the center and on the bottom side to fracturing at the top surface closer to the perimeter. Furthermore, the correlation assumes that there is uniformity of the diamond table composition with the sintering and leaching the same at the center as at the perimeter. The correlation and efficacy of the testing of the prior art methods are further attenuated by other intervening drilling parameters, such as weight on bit (WOB), torque, and rate of penetration (ROP).

Referring to FIGS. 6-9, the present invention is a method and device for determining fracture toughness of a cutting element. The present invention determines a true fracture toughness of a cutting element, such as a polycrystalline diamond compact (PDC) cutter, when the cutting element is under drilling applications. The prior art method relies on a rough correlation of fracturing at the center and bottom side of the diamond table to fracturing at different points across the top surface of the cutting element. The present invention is a more accurate assessment of the cutting element. The fracture toughness determined by the present invention is more indicative of the behavior of the cutting element in a drilling operation. The profile of fracture toughness created by the method of the present invention has more utility and reliability for improving selection of cutters for a drill bit. Fewer intervening drilling parameters affect the correlation of the fracture toughness rating of the present invention to conditions of drilling operations.

Figure 6:
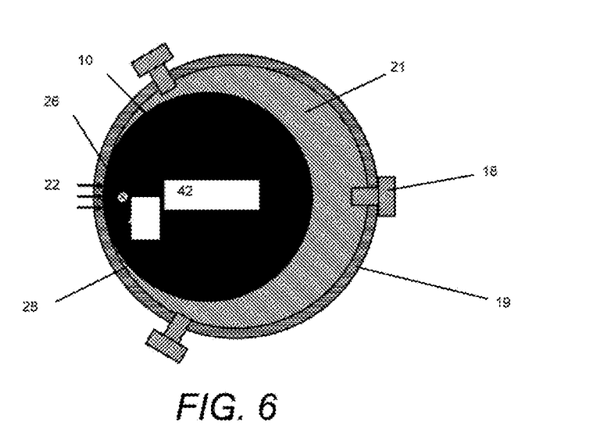
FIG. 6 is a schematic view of a device for determining fracture toughness of a cutting element, according to embodiments of the present invention.
Figure 7:
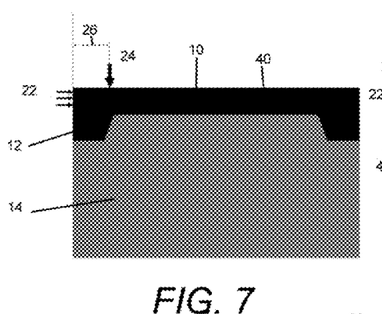
FIGS. 7 and 8 are elevation views of a cutting element being measured using the method of determining fracture toughness according to the present invention.
Figure 8:
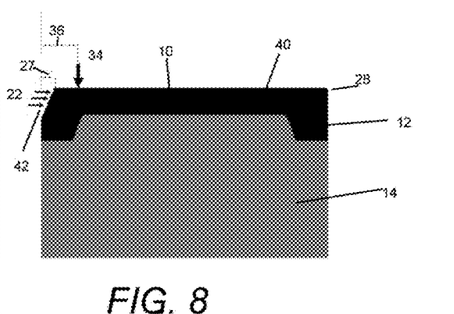

Embodiments of the method of the present invention, as shown in FIGS. 6-9, include an application-specific toughness evaluation of a PDC cutter for downhole drilling. The method can include the steps of: clamping a cutting element 10 into a fixture 18 in a first orientation 20, wherein the cutting element 10 is comprised of a diamond table 12 and a substrate 14; exerting a confining pressure 22 on the diamond table 12; applying a first load 24 at a first distance 26 from a perimeter 28 of the diamond table 12; increasing the first load 24 to a first level sufficient to fracture the diamond table 12; and recording the first level sufficient to fracture the diamond table 12. The method further comprises the steps of removing the cutting element 10 and clamping a second cutting element into the fixture 18 in a second orientation 30. The second cutting element is manufactured under the same conditions as the first cutting element and is comprised of a respective second diamond table and a second substrate. The method includes exerting a second confining pressure on the second diamond table; applying a second load 34 at a second distance 36 from the second perimeter in the second orientation 30; increasing the second load 34 to a second level sufficient to fracture the second diamond table; and recording the second level sufficient to fracture the second diamond table. In some embodiments, the confining pressure 22 has a single direction. FIGS. 6-8 show the confining pressure 22 directed radial to the diamond table 12. The confining pressure 22 can be lateral across top surface 40 of the diamond table 12. The method forms a profile of cutting elements manufactured under the same set of conditions. The data related to distance, load, and level sufficient to fracture each diamond table comprises the profile for that batch of cutting elements.

FIGS. 7 and 8 show an embodiment of the sequence of applying the first load and applying a second load. A first cutter is tested for the first load to fracture. A second cutter is tested for the second load to fracture. The first and second cutters are manufactured under the same conditions, including but not limited to being made in the same batch. FIG. 8 is a variation with a worn edge, while the first distance 26 and second distance 36 are the same. FIGS. 7-8 provide a profile based on toughness of a worn cutter, not just a newly manufactured cutter. Worn cutter data becomes part of the profile for the cutting elements manufactured under the same conditions or in the same batch.

Embodiments can further include repeating the steps of clamping an additional cutting element, exerting an additional confining pressure on the additional diamond table by the fixture, applying an additional load at an additional distance from an additional perimeter of the additional diamond table, increasing the additional load to an additional level sufficient to fracture the additional diamond table, and recording the additional level sufficient to fracture the additional diamond table. The number of additional cutting elements at additional distances can increase the amount of information in a profile created for the batch of cutting elements manufactured under the same conditions. These steps can be repeated at different distances from the perimeter of the diamond table. A profile of the fracture toughness of the cutting element can be compiled from the data comprised of distance, load, and level sufficient to fracture each diamond table.

Figure 9:
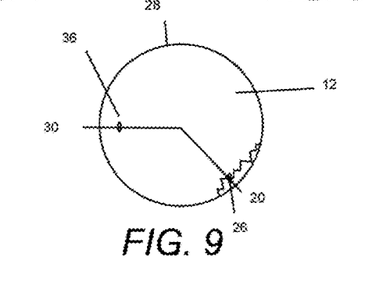
FIG. 9 is a top plan view of a cutting element being measured at a different orientation, according to the present invention.

FIG. 9 is a schematic view of the diamond table 12 of the present invention. The first orientation 20 and the second orientation 30 are different, but shown on the same cutting element 10. The first distance 26 and the second distance 36 are also shown. In the method of the present invention, before the step of applying the second load 34 at the second distance 36, the cutting element 10 is released from the fixture 18, and the cutting element 10 is clamped into the fixture 18 in the second orientation 30. The first orientation 20 is spaced from the second orientation 30. The fracture 40 in the first orientation 20 is isolated from fracture in the second orientation 30. In this embodiment of the method, the same cutting element 10 is used for collecting more than one set of data for a fracture at a first distance. The method does not require a new cutter for each new load and each new fracture, so that the profile is formed more efficiently. A few cutters from a batch of cutters can be used to form the profile and rating for the entire batch. The diamond table 12 in the second orientation 30, and any subsequent orientation, must have the same integrity as the diamond table 12 in the first orientation 20 before fracture. FIG. 9 shows the cutting element 10 rotated from the first orientation 20 at least 90 degrees to the second orientation 30.

The fracture 40 can be observed visually or non-visually. A fracture 40 determined visually includes observation of physical separation of a portion of the PDC cutter from the PDC cutter. A fracture determined non-visually includes observation by a non-destructive-testing method, such as a change in resistance or capacitance of the cutter or imaging internal cracks without physical separation. X-rays and CT imaging are examples of non-destructive techniques to detect a fracture 40.

When the method includes changing orientation, the orientation is changed before each step of applying another load at another distance. The fractures in other orientations are isolated from fracture in any other orientations. As such, the diamond table in the new orientation has the same integrity as the diamond table in any of the other orientations before respective fractures. The method further includes the step of repeating the change in orientation, in addition to the steps of applying another load at another distance, increasing the load to another level sufficient to fracture the diamond table, and recording the another level sufficient to fracture the diamond table. The profile of fracture toughness is further refined to track data of distance, orientation, load, and level sufficient to fracture the diamond table.

In an alternative embodiment to measuring at different distances across the top surface 40 of the diamond table 12, FIG. 8 shows measuring with different worn distances of the diamond table. The toughness of a worn cutter can be incorporated into the profile, instead of only new cutters without wear. In the embodiments of the method incorporating worn distance into the profile of the cutting elements, the second diamond table has a worn edge 42 at a first worn distance 27. The first worn distance 27 can be less than the first distance 26. The second load 34 can start identical to the first load 24, and the second load 34 is still increased to a second level sufficient to fracture the diamond table 12. FIG. 8 shows the second orientation 30 aligned with the edge 42 at the first worn distance 27. The edge 42 can be worn from the perimeter 28 to the first worn distance 27, while the second distance 36 can remain identical to the first distance 26. When worn distance comprises the profile of the cutting elements manufactured under the same set of conditions, the profile is more realistic for the downhole conditions.

Still another embodiment of the present invention is to incorporate worn distances into a profile includes a variation of using the same first cutting element in more than one orientation. Even with the same distances 26 and 36, the orientations cannot be same for a single cutter, since the first orientation 20 already has a fracture. As such, this embodiment of the method includes changing the first orientation 20 to the second orientation 30 with the worn edge. The fracture in the first orientation 20 is isolated from the second orientation 30 with the worn edge, such that the diamond table 12 in the second orientation 30 has the analogous integrity as the diamond table in the first orientation before fracture. The integrity is not identical because of the first worn distance 27, which removed a portion of the diamond table 12.

In this embodiment with worn distance, the orientation and worn distance can be tracked to form a profile with additional data related to the cutting element 10 reacting to being worn. The fracture toughness of the cutting element 10 can be rated with further pertinent information for a drilling operation. The steps of applying another load, increasing load to another level sufficient to fracture the diamond table, and recording the level sufficient to fracture the diamond table can be repeated with different worn distances. Before the step of applying another load, the edge of the cutting element can be worn to another worn distance.

The profile of the cutting element is now formed with data comprised of distance, orientation, worn distance, load, and level sufficient to fracture the diamond table.

Figure 10:
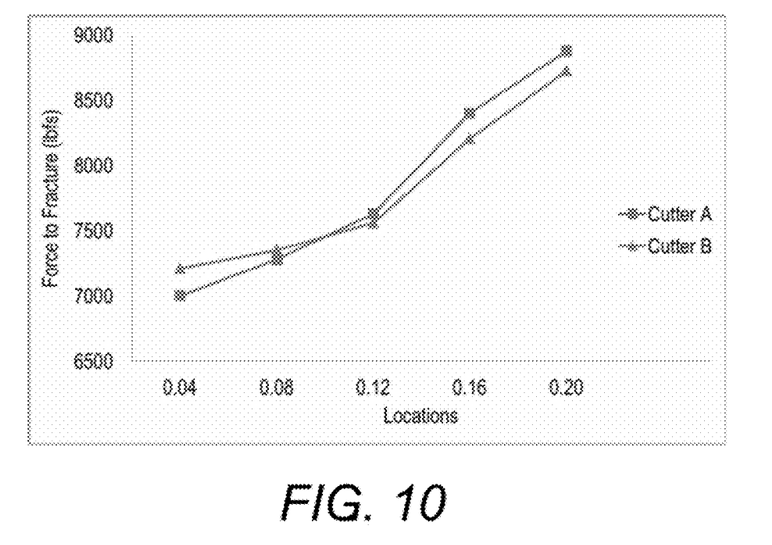
FIG. 10 is a graph illustration showing level of force to fracture and distance from perimeter of the diamond table, according to the method of the present invention.

FIG. 10 shows a graph illustration of the method of the present invention. The profiles of two cutters are shown according to force of fracture or level sufficient to fracture and locations or distance from the perimeter. Cutter A is weaker than Cutter B at distances closer to the perimeter, but Cutter A is stronger than Cutter B at distances further from the perimeter. The method of the present invention provides a profile unlike the prior art methods. The information and profile is more accurate and useful for selecting a cutter measured by the present invention. The correlation of the toughness at the center would not have revealed the progression of fracture toughness across the top surface. Cutter B could be more properly selected over Cutter A for placement on an outer portion of the drill bit, which does not cut as deep. The impact forces at the less deep cut are closer to the perimeter, and Cutter B is stronger than Cutter A at these distances closer to the perimeter.

Figure 11:
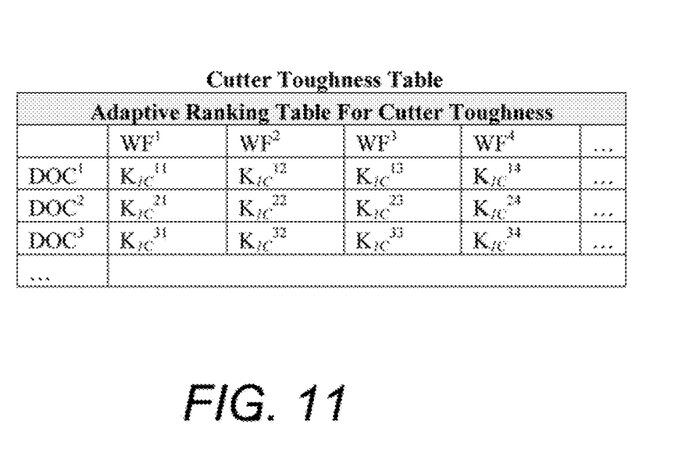
FIG. 11 is a chart illustrations showing a profile of fracture toughness of a cutter based on an embodiment of the method of the present invention.

Similarly, FIG. 11 shows a chart illustration for Cutter Toughness. The adaptive rankings are shown for a more complete profile. There are four different worn distances (WF), and there are three different distances from the perimeter (DOC). The fracture force or level sufficient to fracture (K1C) values are charted in relation to worn distance and distance from perimeter. This adaptive ranking is possible through the method of the present invention. The amount of wear affects fracture toughness according to the distance from perimeter. For example, from FIG. 11, the cutting element with an impact force at DOC3 and worn to WF4 has fracture toughness K1C33. Cutting elements at the tips of the drill bit would be subject to more wear, so the worn distance WF will be more relevant. A cutting element to be set at the tip of the drill bit can be screened for a high fracture toughness K1C at the higher worn distances WF3 and WF4.

Embodiments of the present invention also include a device for determining fracture toughness, according to the method of the present invention. The device comprises a fixture 18, a clamp 19, a means for exerting a confining pressure 22, and a loading means for loads 24, 34. The fixture 18 holds a cutting element 10 comprised of a diamond table 12 and a substrate 14. The fixture 18 can be a ring or vice. The clamp 19 is mounted on the fixture 18 and has a spacer 21. The clamp 19 is shown with screw actuable to squeeze the spacer 21 against the cutting element 10. The cutting element 10 mounts in the clamp 19 adjacent to the spacer 21 in a first orientation 20. The spacer 21 and cutting element 12 have complementary profiles for a stable arrangement in the clamp 19. The interior of the clamp 19 is tangent to the cutting element. The means for exerting a confining pressure 22 can be radial to clamp 19, or radial to cutting element 12 or both. The confining pressure 22 has a single direction and can be lateral across a top surface 40 of the diamond table 12. The loading means exerts force to fracture at the first distance 26 from the perimeter 28 of the diamond table 12. The loading means is moveable to a second distance 36 from the perimeter 36 and to any other distance from the perimeter 28. FIG. 8 shows the cutting element 12 having a worn distance 27 from the perimeter 28 to a worn edge 42. The distance from perimeter to worn edge is less than distance from perimeter to first distance, and the edge can become more and more worn for different measurements. The orientations will also change as the fracture in one orientation requires rotation of the cutting element to get a clean reading of the force to fracture in the new orientation. Embodiments of the device of the present invention may also include a means for recording data comprised of distance, orientation, worn distance, load, and level sufficient to fracture the diamond table and a means for forming a profile of the cutting element with the data. A computer processor or other prior art equipment may be available to enter, store, arrange and modify this data.

The method for determining fracture toughness of a cutting element according to the present invention measures distance, load, and level sufficient to fracture the diamond table. The loads are determined at different distances from the perimeter of the diamond table. Prior art tests assume uniformity of the hard substance to be tested. The drilling operations include cutters with known non-uniformity due the the nature of the sintering process used to form the cutter. The present invention directly addresses this failing of the prior art testing methods. As the loads are applied at different distances, the method of the present invention further includes changing orientation on the cutting element. Instead of testing a new distance on a new cutting element, the amount of waste for tested cutting elements is reduced. Different positions on the cutting element are tested to more realistically assess fracture toughness across the top surface of the cutting element, as in a drilling operation. The method and device can rate fracture toughness of cutting elements for assembling a drill bit. The fracture toughness at different positions allow selection of cutting elements for placement on the drill bit for the more specific stronger fracture toughness at a particular distance from the perimeter.

The present invention also provides a method and device for determining fracture toughness of a cutting element, when the cutting element is worn. The profile from the tested cutting elements is compiled to form a more complete profile of fracture toughness of cutting elements manufactured under the same conditions, such as having been formed by a particular sintering and leaching processes under particular heat and pressure conditions. The profile can be accurate and relevant to the class of cutters, including cutters made in the same batch with the same sintering and leaching.

Drilling operations degrade the cutting element, and the fracture toughness can change, depending upon the amount of wear. The prior art methods of testing do not account for these changes, so the ratings and profiles of the prior art toughness standards are too roughly correlated to actual fracture toughness in a drilling operation. Intervening drilling parameters, such as weight on bit (WOB), torque, and rate of penetration (ROP), further skew the prior art methods from reliable and accurate assessment of fracture toughness of a cutting element. The method of the present invention varies the worn distance, the amount of wear on the edge of the diamond table from the perimeter. The worn distance becomes another factor in the profile. The worn distance and distance from the perimeter for applying the load are varied to form the more complete profile of fracture toughness. Additionally, the method of the present invention includes the affect of orientation on the cutting element, as orientation can interact with worn distance and distance from the perimeter. The method and device of the present invention disclose a more predictive and useful profile of fracture toughness of the cutting element formed with data comprised of distance, orientation, worn distance, load, and level sufficient to fracture the diamond table.

The foregoing disclosure and description of the invention is illustrative and explanatory thereof. Various changes in the details of the illustrated structures, construction and method can be made without departing from the true spirit of the invention.

We claim:

1. A method for determining fracture toughness of a cutting element, comprising the steps of:
   clamping a first cutting element into a fixture in a first orientation, said first cutting element being comprised of a first diamond table and a first substrate;
   exerting a first confining pressure on said first diamond table by said fixture, said confining pressure being radial to said first diamond table and across a first top surface of said first diamond table;

applying a first load at a first distance from a first perimeter of said first diamond table;

increasing said first load to a first level sufficient to fracture said first diamond table;

recording said first level sufficient to fracture said first diamond table;

clamping a second cutting element into said fixture in a second orientation, said second cutting element being comprised of a second diamond table and a second substrate, said first cutting element and said second cutting element being manufactured under a same set of conditions;

exerting a second confining pressure on said second diamond table by said fixture, said second confining pressure being radial to said second diamond table and across a second top surface of said second diamond table;

applying a second load at a second distance from a second perimeter of said second diamond table;

increasing said second load to a second level sufficient to fracture said second diamond table;

recording said second level sufficient to fracture said second diamond table; and forming a profile of cutting elements manufactured under said same set of conditions as said first cutting element and said second cutting element, said profile being comprised of data related to distance, load, and level sufficient to fracture said first diamond table and said second diamond table.

2. The method for determining fracture toughness, according to claim 1, further comprising the steps of:

clamping an additional cutting element into said fixture in an additional orientation, said additional cutting element being comprised of an additional diamond table and an additional substrate, said first cutting element, said second cutting element, and said additional cutting element being manufactured under a same set of conditions;

exerting an additional confining pressure on said additional diamond table by said fixture, said additional confining pressure being radial to said additional diamond table and across an additional top surface of said additional diamond table;

applying an additional load at an additional distance from an additional perimeter of said additional diamond table;

increasing said additional load to an additional level sufficient to fracture said additional diamond table; and recording said additional level sufficient to fracture said additional diamond table, wherein said step of forming said profile of cutting elements manufactured under said same set of conditions comprises data related to distance, load, and level sufficient to fracture said additional diamond table.

3. The method for determining fracture toughness, according to claim 2, further comprising the steps of:

repeating the steps of clamping an additional cutting element at an additional orientation, exerting an additional confining pressure on said additional diamond table by said fixture, applying an additional load at an additional distance from an additional perimeter of said additional diamond table, increasing said additional load to an additional level sufficient to fracture said additional diamond table, and recording said additional level sufficient to fracture said additional diamond table, wherein said step of forming said profile of cutting elements manufactured under said same set of conditions comprises data related to distance, load, and level sufficient to fracture additional diamond tables.

4. The method for determining fracture toughness, according to claim 3, wherein at least one additional diamond table has at least one additional worn edge at at least one additional worn distance along at least one additional perimeter, said at least one additional confining pressure being exerted on said at least one additional worn edge, and wherein said profile further comprises at least one additional worn distance.

5. The method for determining fracture toughness, according to claim 2, wherein said additional diamond table has an additional worn edge at an additional worn distance along said additional perimeter, said additional confining pressure being exerted on said additional worn edge, and wherein said profile further comprises said additional worn distances.

6. The method for determining fracture toughness, according to claim 1, wherein said second diamond table has a worn edge at a first worn distance along said second perimeter, said second confining pressure being exerted on said worn edge, said first worn distance being less than said first distance, and wherein said profile further comprises said first worn distance.

7. A method for determining fracture toughness of a cutting element, comprising the steps of:

clamping a first cutting element into a fixture in a first orientation, said first cutting element being comprised of a first diamond table and a first substrate;

exerting a first confining pressure on said first diamond table by said fixture, said confining pressure being radial to said first diamond table and across a first top surface of said first diamond table;

applying a first load at a first distance from a first perimeter of said first diamond table;

increasing said first load to a first level sufficient to fracture said first diamond table;

recording said first level sufficient to fracture said first diamond table;

releasing said first cutting element from said fixture;

re-clamping said first cutting element into said fixture in a second orientation, said first orientation being spaced from said second orientation;

exerting a second confining pressure on said first diamond table by said fixture, said second confining pressure being radial to said first diamond table and across said first top surface of said first diamond table;

applying a second load at a second distance from said first perimeter of said first diamond table;

increasing said second load to a second level sufficient to fracture said first diamond table a second time;

recording said second level sufficient to fracture said first diamond table said second time; and forming a profile of cutting elements manufactured under said same set of conditions as said first cutting element, said profile being comprised of data related to distance, load, and level sufficient to fracture said first diamond table, wherein fracture in said first orientation is isolated from fracture in said second orientation.

8. The method for determining fracture toughness, according to claim 7, said first diamond table in said second orientation having a same integrity as said first diamond table in said first orientation before fracture in said first orientation.

9. The method for determining fracture toughness, according to claim 7, further comprising the step of:
rotating said first cutting element at least 90 degrees from said first orientation to said second orientation.

10. The method for determining fracture toughness, according to claim 7, further comprising the steps of:
repeating the steps of releasing said first cutting element; re-clamping said first cutting element at an additional orientation, exerting an additional confining pressure on said first diamond table by said fixture, applying an additional load at an additional distance from said first perimeter of said first diamond table, increasing said additional load to an additional level sufficient to fracture said first diamond table, and recording said additional level sufficient to fracture said first diamond table at said additional orientation,
wherein said step of forming said profile of cutting elements manufactured under said same set of conditions comprises data related to distance, load, and level sufficient to fracture said first diamond table at additional orientations.

11. The method for determining fracture toughness, according to claim 10, wherein said first diamond table has an additional worn edge at an additional worn distance along said first perimeter, said additional confining pressure being exerted on said additional worn edge, and
wherein said profile further comprises said additional worn distance.

12. The method for determining fracture toughness, according to claim 11, said first diamond table in said second orientation having a same integrity as said first diamond table in said first orientation before fracture in said first orientation.

13. The method for determining fracture toughness, according to claim 11, further comprising the step of:
rotating said first cutting element at least 90 degrees from said first orientation to said second orientation.

14. The method for determining fracture toughness, according to claim 7, wherein said first diamond table has a worn edge at a first worn distance along said first perimeter at said second orientation, said first confining pressure being exerted on said worn edge, said first worn distance being less than said first distance, and
wherein said profile further comprises said first worn distance.

15. A device for determining fracture toughness, comprising:
a fixture holding a cutting element, said cutting element being comprised of a diamond table and a substrate;
a clamp comprised of a spacer, said cutting element being mounted in said clamp adjacent to said spacer in a first orientation, said clamp being mounted on said fixture, said space having a complementary profile to said cutting element so as to fit in said fixture;
means for exerting a confining pressure on said diamond table, said confining pressure being radial to said cutting element and lateral across a top surface of said diamond table; and
a load bearing means at a first distance from a perimeter of said diamond table,
wherein said load bearing means is moveable to a second distance from said perimeter.

16. The device for determining fracture toughness, according to claim 15, said cutting element having a worn edge, wherein distance from perimeter of said diamond table to worn edge less than distance from said perimeter to first distance, said cutting element being in a second orientation.

17. The device for determining fracture toughness, according to claim 15, said cutting element having another worn edge, wherein distance from perimeter to another worn edge less than distance from perimeter to another distance, said cutting element being in another orientation.

18. The device for determining fracture toughness, according to claim 15, said cutting element having a second orientation relative to said means for exerting a confining pressure, said first orientation being spaced from said second orientation, wherein fracture in said first orientation is isolated from fracture in said second orientation, said diamond table in said second orientation having a same integrity as said diamond table in said first orientation before fracture.

19. The device for determining fracture toughness, according to claim 15, further comprising:
means for recording data comprised of distance, orientation, worn distance, load, and level sufficient to fracture said diamond table.

20. The device for determining fracture toughness, according to claim 15, further comprising:
means for forming a profile of said cutting element with said data, said
profile corresponding to cutting elements manufactured under same conditions as said cutting element.

* * * * *